United States Patent [19]

Succi et al.

[11] Patent Number: 5,294,378
[45] Date of Patent: Mar. 15, 1994

[54] CALIBRATING APPARATUS FOR ISOTHERMALLY INTRODUCING MOISTURE INTO A STREAM OF DRY GAS AT A VERY SLOW RATE

[75] Inventors: Marco Succi; Carolina Solcia; Antonio Coppola, all of Milan, Italy

[73] Assignee: S.A.E.S. Getters SpA, Milano, Italy

[21] Appl. No.: 18,226

[22] Filed: Feb. 16, 1993

[30] Foreign Application Priority Data

May 26, 1992 [IT] Italy .................. MI 92 A 001299

[51] Int. Cl.$^5$ .............................................. B01F 3/04
[52] U.S. Cl. .................................. 261/130; 261/131;
  261/63; 261/153; 261/104
[58] Field of Search ............... 261/130, 131, 63, 153, 261/104

[56] References Cited

U.S. PATENT DOCUMENTS

| | | |
|---|---|---|
| 3,856,204 | 12/1974 | Chand . |
| 4,086,305 | 4/1978 | Dobritz .................. 261/104 |
| 4,110,419 | 8/1978 | Miller ..................... 261/104 |
| 4,399,942 | 8/1983 | Chand . |
| 4,419,302 | 12/1983 | Nishino et al. .......... 261/104 |
| 4,436,674 | 3/1984 | McMenamin ............ 261/130 |
| 4,618,462 | 10/1986 | Fisher et al. ............. 261/130 |
| 4,652,408 | 3/1987 | Montgomery ........... 261/104 |
| 4,674,494 | 6/1987 | Wiencek .................. 261/104 |
| 4,750,483 | 6/1988 | Ankartross et al. ..... 261/130 |
| 4,800,000 | 1/1989 | Zatko et al. . |
| 4,861,524 | 8/1989 | Sielaff et al. ............ 261/130 |

FOREIGN PATENT DOCUMENTS 0307265 3/1989 European Pat. Off. .

OTHER PUBLICATIONS

Mikokami et al "Measurement of Trace Moisture in High Purity Gases with the Standard Moisture Generator (MG-10)" Microcontamination Conference Proceedings, Oct. 16-18, Cannon Communications, Inc., pp. 168-180.

*Primary Examiner*—Tim Miles
*Attorney, Agent, or Firm*—David R. Murphy

[57] ABSTRACT

A calibrating apparatus for isothermally introducing, into a stream of dry gas, amounts of moisture lower than 1000 ppb, said apparatus comprising:

A. a moist gas generating unit, comprising in its turn:
  i) a cylindrical shell;
  ii) a permeation module, inside said cylindrical shell, containing water and comprising a peripheral membrane;
  iii) a thermal conditioner, arranged too inside said cylindrical shell, upstream of said permeation module;
B. an isothermal heat sink, thermally connected to the outside surface of said cylindrical shell, wherein said moist gas generating unit, under item A), is lodged in a recess of said heat sink;
C) a heat radiator;
D) a Peltier heater-cooler, thermally arranged between said isothermal heat sink (under item B) and said heat radiator (under item C).

10 Claims, 1 Drawing Sheet

CALIBRATING APPARATUS FOR ISOTHERMALLY INTRODUCING MOISTURE INTO A STREAM OF DRY GAS AT A VERY SLOW RATE

FIELD OF THE INVENTION

The invention relates to a calibrating apparatus for isothermally introducing moisture into a stream of dry gas at a very slow rate and relates too, in a more general way, to a water vapor generating apparatus for calibrating analyzers or the like.

THE PRIOR ART

U.S. Pat. No. 3,856,204 discloses an apparatus for the emission of a gas or vapor, at a constant rate, into a driving fluid medium, as to produce an accurately known concentration of the gas in the fluid medium. The gas is held in a pressure vessel (cylinder), in equilibrium with its liquid phase or solely in its gaseous phase, and permeates through a permeable material (poly dimethyl-siloxane), filling an accurately dimensioned passage through one end of the cylinder; it also discloses the use of such a device in an apparatus for the analysis of fluid mixtures.

The same U.S. Pat. No. 3,856,204 states that such disclosed apparatus has characteristically low overall sensitivity to temperature variations. The Applicants, on the contrary, discovered a new apparatus, containing, among others, a different kind of membrane, which is fairly dependent on temperature variations without impairing the accuracy of the measurement; such a new apparatus therefore permits a quite satisfactory increase in the range of variability of the water (moisture) emission rate. By shifting the temperature from 5° to 70° C. or viceversa, for instance, the amount of released moisture can increase or decrease even 100 times. Moreover the peculiar structure of the new apparatus brings about other advantages which will be hereinafter pointed out.

U.S. Pat. No. 4,399,942 discloses a device which comprises two chambers, the one for holding the substance in a liquefied form, and the other for holding it solely in a gaseous or vapor form. The substance permeates through a permeable material, between the two chambers, and then through another permeable material at the outlet from the second chamber. A constant temperature is maintained around the cylinder in order to maintain a constant emission rate of the substance contained in said cylinder.

European Patent Application 0 307 265 states that when using a two-chamber device, sold for water vapour (moisture) permeation, of the type described in the above U.S. Pat. No. 4,399,942, the pressure of the driving fluid medium, such as a dry gas, lapping the permeable material (poly-dimethyl-siloxane) through which the water vapor permeates, has a certain impact on the permeation rate; a correction of this pressure effect is disclosed.

In an article "Measurement of Trace Moisture in High Purity Gases with the Standard Moisture Generator (MG - 10)" by Mizokami, K. et al., published in Microcontamination 1991 Conference Proceedings (by Canon Communications, Inc.), there is described a standard moisture generator for the calibration of an APIMS (Atmospheric Pressure Ionization Mass Spectrometer). However such a moisture generator uses a two-step dilution system after moisture has been introduced into the stream of dry gas. Manipulation of the calibrating gas, once it has been doped with a given amount of moisture, leads to uncertainties as to the amount or the level of doping. To allow for this manipulation extra lengths of tube must be used, which can lead to additional sources of error especially as these lengths must be kept at a high temperature level to stop moisture adhesion to the tube surfaces. As these surfaces have to be carefully electro-polished, additional expense is incurred. Furthermore it is described how such devices are linear only up to 200 ppb of moisture content. Other moisture generators used several moisture producing devices in parallel, each with its own oven to produce a range of moisture concentrations.

It is of course well known that it is always necessary, in the semiconductor industry, to accurately measure the concentration of impurities, such as water vapor (moisture) in the gases used during the manufacture of integrated circuits. Particularly it is necessary to accurately calibrate analyzers, such as hygrometers, in the range of less than 1000 ppb and especially, more recently, of less than 10 ppb, or even 1 ppb, in a reliable, economical and easy way.

OBJECTS OF THE INVENTION

Accordingly it is one object of the present invention to provide an apparatus for accurately introducing moisture into a stream of dry gas, which apparatus is substantially free of one or more of the problems of the prior apparatuses.

Another object of the present invention is to provide an apparatus for accurately introducing moisture into a stream of dry gas, which apparatus is reliable, economical and easy to use.

A further object of the present invention is to provide an apparatus for accurately introducing moisture into a stream of dry gas, which apparatus does not require further manipulation of the doped gas.

Another object of the present invention is to provide an apparatus for accurately introducing moisture into a stream of dry gas, which apparatus does not require excessive lengths of electro-polished tube.

A still further object of the present invention is to provide an apparatus for accurately introducing moisture into a stream of dry gas, which apparatus is capable of introducing moisture in amounts of less than 1000 ppb and even as low as 1 ppb.

DISCLOSURE OF THE INVENTION

The above and other objects of the invention are accomplished, according to the present invention, by providing a calibrating apparatus for isothermally introducing, into a stream of dry gas, calibrated amounts of moisture, lower than 1000 and even 1 ppb, said apparatus comprising:

A. a moist gas generating unit, comprising in its turn:
  i) a cylindrical shell, having an inside surface and having too an inlet opening (for said stream of dry gas) and an outlet opening (for the corresponding desired stream of moist gas);
  ii) a permeation module, inside said cylindrical shell, containing water and comprising a peripheral membrane, made from a polymeric fluorinated material, which is tangentially lapped by the dry gas to be moistened;
  iii) a thermal conditioner, arranged inside said cylindrical shell, upstream of said permeation module;

B. an isothermal heat sink, thermally connected to the outside surface of said cylindrical shell, wherein said heat sink has a cylindrical recess therein, as well as a planar heat conducting surface, and wherein said moist gas generating unit, under item A), is lodged in said recess of said heat sink;

C. a heat radiator;

D. a Peltier heater-cooler, thermally arranged between said isothermal heat sink (under item B) and said heat radiator (under item C), wherein said Peltier heater-cooler does transfer heat from said isothermal heat sink to said heat radiator or vice-versa.

The calibrating apparatus hereinabove may also, furthermore, comprise:

E. means for passing the dry gas through said moist gas generating unit;

F. means for controlling the flow rate of the dry gas;

G. means for controlling the temperature of said Peltier heater-cooler.

Said polymeric fluorinated material may be for instance consisting of one or more polymers or copolymers of fluorine containing or fluorine free polymerizable monomers, like ethylene, propylene, tetrafluoroethylene, hexafluoropropylene, vinylidene fluoride, chlorofluorinated ethylenes and/or propylenes, mixtures, blends and compounding products thereof and similar, provided that at least one of the monomers be a fluorine containing monomer.

Said isothermal heat sink may be a metal body and said heat radiator may be made from metal.

The apparatus according to the invention may comprise means for passing an electrical current through the Peltier heater-cooler in a first direction, in order to heat the moist gas generating unit; additionally the same apparatus may comprise also means for passing an electrical current through the Peltier heater-cooler in a second direction, in order to cool the same moist gas generating unit.

If the calibrating apparatus according to the invention has to introduce moisture amounts lower than 10 or even 1 ppb into a dry gas at superatmospheric pressure, the best results are reached when:

said permeation module, under item A/ii, is a tube eccentric or coaxial, with respect to said cylindrical shell under item A/i;

said thermal conditioner, under item A/iii, is consisting of an open porous structure, made from aluminum, thermally connected to said inside surface of said cylindrical shell;

said heat radiator, under item C) has a planar heat conducting surface parallel to and positioned a distance from the planar heat conducting surface of said isothermal heat sink;

said Peltier heater-cooler has a first and second parallel heat transfer surfaces thermally arranged between the isothermal heat sink and the radiator, with the first heat transfer surface in contact with the radiator and the second heat transfer surface in contact with the isothermal heat sink; wherein electrical current, passing through the Peltier heater-cooler in either of the two directions heats one surface of the heater-cooler and cool the other surface of the heater-cooler or vice versa.

By passing an electrical current in either direction through said Peltier heater-cooler, it is possible to accurately keep the isothermal heat sink at prefixed constant temperature selected in a very wide range (from 0° to 70° C.).

The apparatus of the present invention can be used to introduce, accurately minute amounts of moisture into a stream of any dry gas that does not react with moisture. Examples of such gases are, among others, the noble gases (in particular argon and helium), hydrogen, oxygen, nitrogen, carbon monoxide and dioxide, methane, other hydrocarbon gases and similar. These gases, doped with the minute amounts of moisture, can be advantageously used for the calibration of other water or moisture analyzers, such as hygrometers, APIMS or analyzers based on cells, as described in U.S. Pat. No. 4,800,000.

The invention may be better understood now by reference to the following description of the drawings.

DETAILED DESCRIPTION OF THE INVENTION

Figure 1:
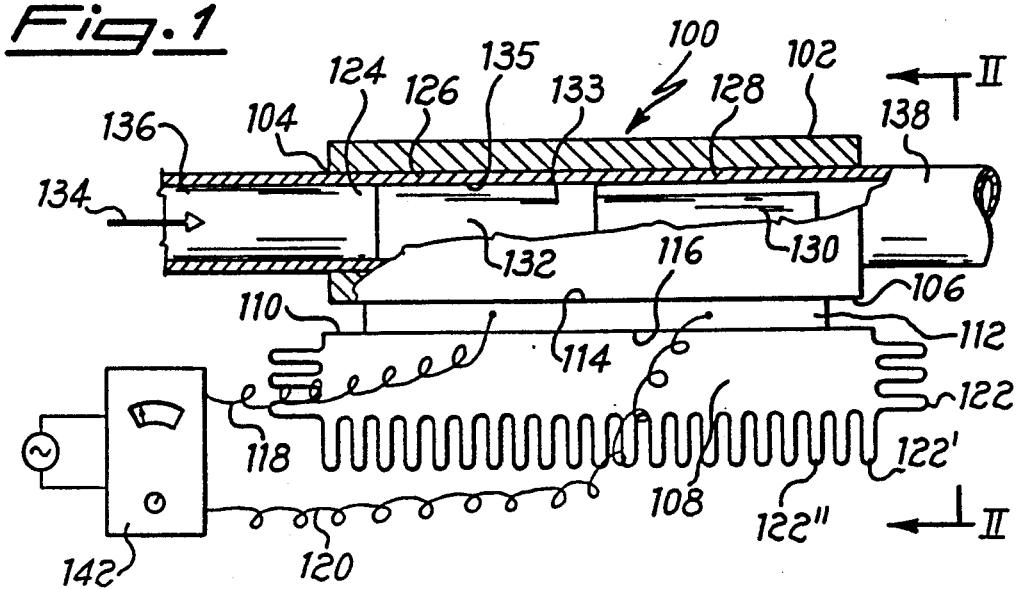
FIG. 1 is a partially cut away top view of an apparatus according to the present invention.
Figure 2:
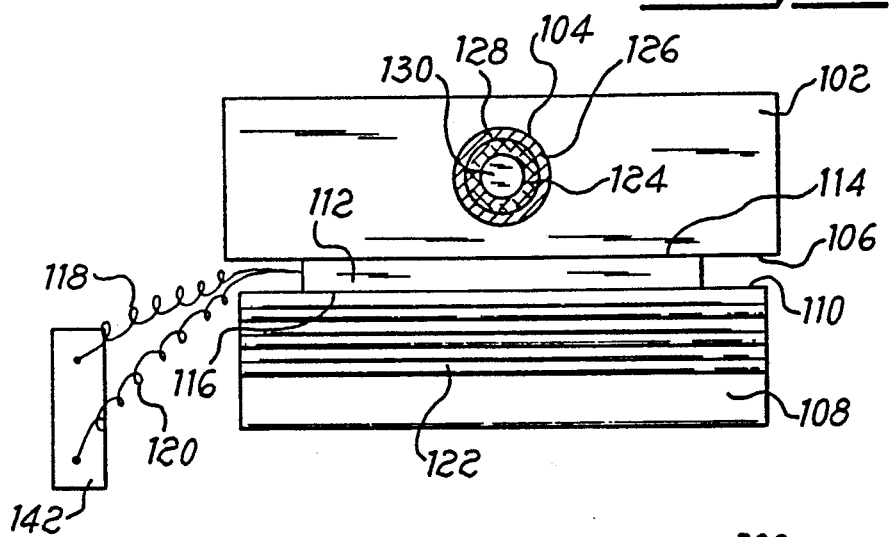
FIG. 2 is a sectional view taken along line II—II of FIG. 1.

Referring now to the drawings and in particular FIGS. 1 and 2 there is shown a calibrating apparatus 100 for accurately and isothermally introducing moisture into a stream of dry gas. The apparatus 100 has a metal isothermal heat sink 102, provided with a cylindrical recess 104 and with a planar heat conducting surface 106.

The apparatus 100 is provided with a metal radiator 108 having a planar heat conducting surface 110 parallel to and positioned a distance from the planar heat conducting surface 106 of the isothermal heat sink 102.

The apparatus 100 is furtherly provided with a Peltier heater-cooler 112 which has a first heat transfer surface 114 parallel to the heat conducting surface 106 of the heat sink 102; and has a second heat transfer surface 116 parallel to the heat conducting surface 110 of the metal radiator 108. Thus the heat transfer surfaces 114, 116 of the heater cooler 112 are thermally disposed between the heat conducting surface 106 of the isothermal heat sink 102 and the heat conducting surface 110 of the radiator 108; the heat transfer surface 116 is in contact with the radiator 108 and the heat transfer surface 114 is in contact with isothermal heat sink 102.

Direct electrical current passes through the Peltier heater-cooler 112 in either of the two directions by means of the conductors 118, 120. In one direction heat is transferred from surface 114 to surface 116; in the other direction heat is transferred from surface 116 to surface 114. By selecting the current direction it is possible to heat one surface (114 or 116) and to cool the other surface (116 or 114). By passing now the current in either direction through the heater-cooler 112 it is possible to keep accurately the isothermal heat sink 102 at its desired (constant) temperature level selected in a very wide range (from 0° to 70° C.). Heat is transferred to or from the surroundings by conduction, convection and radiation, all of which can be promoted by fins arranged on the radiator such as fins 122, 122', 122". . .

The calibrating apparatus 100 is also provided with a moist gas generating unit 124, comprising a cylindrical shell 126 in the form of a tube 128. Tube 128 is lodged in the recess 104 of the isothermal heat sink 102. Within cylindrical shell 126 and coaxial therewith there is a water permeation module 130 and a thermal conditioner 132, upstream of the module. Thermal conditioner 132 is consisting of a substance showing high thermal conductivity, to stabilize the temperature of the dry gas before being doped with moisture. Thermal conditioner 132 is preferably made from metal and has an open porous structure, such that the dry gas quickly comes into thermal equilibrium with its surroundings. The metal should have a high thermal conductivity and it can advantageously be aluminium in the form of small pieces, chips, thin rods, small balls or the like, arranged in a space 133 within cylindrical shell 126 and in thermal contact with the inside surface 135 of tube 128. Thermal conditioner 132 is adjacent to the water permeation module 130, upstream of the same module (see arrow 134).

Moist gas generating unit 124 is in thermal contact with the isothermal heat sink 102; therefore the moist gas generating unit 124 and the heat sink 102 always have the same temperature. The moist gas generating unit 124 has a dry gas inlet 136 and a moist gas outlet 138 for passing the dry gas through the moist gas generating unit 124 and over the water permeation module 130. The water permeation modules tested by the applicants (see the examples) are well known in the art since more than 20 years and a short hint to their existence is already retrievable, for instance, in U.S. Pat. No. 3,856,204 (column 1, lines 11-14). The flow rate of the dry gas is controlled by a device illustrated in FIG. 3, with the temperature of the Peltier heater-cooler 112 being controlled by means of an electrical circuit 142.

Figure 3:
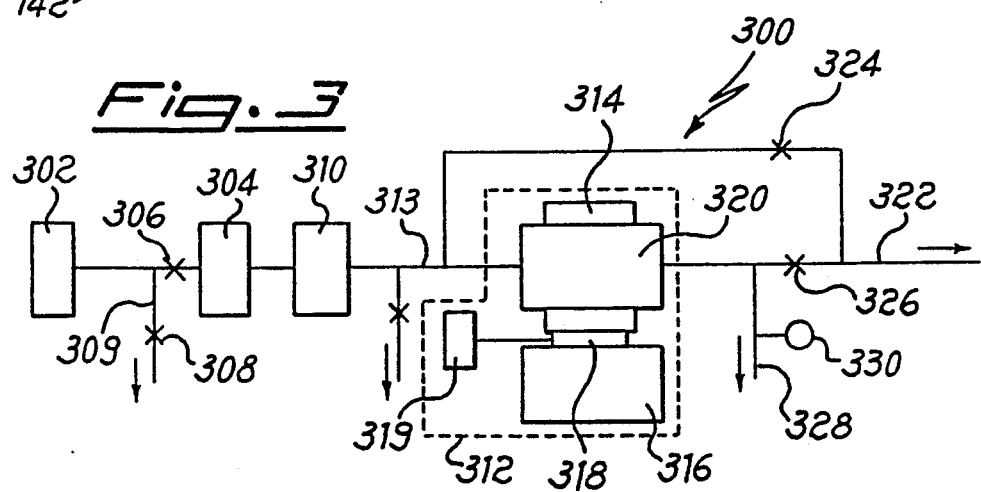
FIG. 3 is a block diagram showing a system (packaging) comprising an apparatus according to the present invention.

Referring now to FIG. 3 there is shown a block diagram of a calibration device 300 in which there is a gas source 302, preferably maintained at superatmospheric pressure. However in the broadest aspects of the present invention the pressure of the gas can be subatmospheric as long as there is a pressure difference sufficient for the gas to flow through the calibration device 300. Gas source 302 is in fluid communication with a mass flow controller 304 for measuring and controlling the flow rate of gas through device 300. Valve 306 controls the inlet of the gas, whereas valve 308 in a conduit 309 allows gas to be purged to the atmosphere in order to aid the installation of the calibration device 300. Flow controller 304 is in fluid communication with the gas purifier 310. Gas purifier 310 is required to ensure a moisture free or dry feed gas for apparatus 312, which is represented in more detail by apparatus 100 of FIGS. 1 and 2. Purifier 310 may be filled with a molecular sieve material if the gas is hydrogen or oxygen. As a result, the moisture content of the dry gas can be as low as 0.5-1.0 ppb. A getter material, such as the ones traded as St 707 or St 198 and described in U.S. Pat. Nos. 4,312,669 and 4,306,887 respectively, may be used if an inert gas (noble gases or nitrogen) is employed. When a getter material is used, a level of moisture of less than 0.1 ppb is ensured in the stream of dry gas. The gas purifier 310 is connected by means of a dry gas inlet 313, to the apparatus 312, comprising an isothermal heat sink 314, a radiator 316 and a Peltier heater-cooler 318, provided with temperature controlling means 319. The moist gas generating unit 320, in thermal contact with heat sink 314, has a moist gas outlet 322.

In order to avoid an excessive accumulation of moisture when the apparatus 312 is generating dry gas, valves 324, 326 can be operated to produce a by-pass of dry gas but a constant flow of gas through moist gas generating unit 320. The excess of moisture containing gas is discharged through conduit 328, to air, for instance.

The Peltier heater-cooler 112 can be supplied by different manufacturers, for instance by the U.S.A. firm Materials Electronic Products Corp. 994, trading such heater-coolers as "Frigichip". These heater-coolers are described for instance in a publication entitled "Frigichip Miniature Ceramic Modules". A particularly useful heater-cooler is the Frigichip catalogue number "CP 1.4-71-06L".

By changing the flow rate of the gas from 1 to 10 l /minute and the temperature of the heat sink from 70° C. to 0° C. the output of moist gas can be from 1000 ppb down to 1 ppb of moisture content.

EXAMPLE

A calibration device was set up according to the block diagram 300 of FIG. 3. The gas source was a cylinder of nitrogen at superatmospheric pressure. A gas purifier, filled with a $Zr_2Fe$ alloy, and working at 100° C., reduced the moisture content of the inlet gas to less than 0.1 ppb.

The permeation module, coaxially lodged in the cylindrical shell of the moist gas generating unit, traded as HRT, had been purchased from the KIN-TEK Laboratories (outer diameter = ¼ i.e. 6.4 mm; total length = 8 cm; active length = 3 cm; membrane material = TFE i.e. fluorinated polymeric material). The porous heat conditioner was made from aluminium.

The Peltier heater-cooler was kept at the desired constant temperature and the gas flow rate was maintained at a fixed value. The moisture content of the outlet gas was both measured and calculated from the flow rate of the gas (from the emission rate of the water permeation tube, said rate being supplied by KIN-TEK as a function of temperature), giving thus rise to the following two series of nearly identical results.

| Gas flow rate Standard liter per minute | Temperature °C. | Moisture in the gas (ppb) | |
|---|---|---|---|
| | | Calculated | Measured |
| 10 | 6 | 1 | 1 |
| 4 | 10 | 6,4 | 6,4 |
| 4 | 30 | 31 | 30 |
| 4 | 40 | 64 | 63 |
| 4 | 50 | 125 | 125 |
| 1 | 47 | 200 | 202 |
| 1 | 58 | 500 | 498 (*) |
| 0.5 | 50 | 1000 | 1005 (*) |

(*) These two values were measured by means of a cell, as described in U.S. Pat. No. 4,800,000; all other measurements were made using an APIMS.

Although the invention was described in considerable detail with respect to a preferred embodiment thereof, it will be understood that variations and modifications can be made without departing from the spirit and the scope of the same invention.

What is claimed is:

1. A calibrating apparatus for isothermally introducing, into a stream of dry gas, calibrated amounts of moisture, lower than 1000 and even 1 ppb, said apparatus comprising:

A. a moist gas generating unit, comprising in its turn:

i) a cylindrical shell, having an inside surface and having too an inlet opening (for said stream of dry gas) and an out let opening (for the corresponding desired stream of moist gas);
ii) a permeation module, inside said cylindrical shell, containing water and comprising a peripheral membrane, made from a polymeric fluorinated material, which is tangentially lapped by the dry gas to be moistened;
iii) a thermal conditioner, arranged too inside said cylindrical shell, upstream of said permeation module;

B. an isothermal heat sink, thermally connected to the outside surface of said cylindrical shell, wherein said heat sink has a cylindrical recess therein, as well as a planar heat conducting surface, and wherein said moist gas generating unit, under item A), is lodged in said recess of said heat sink;

C) a heat radiator;

D) a Peltier heater-cooler, thermally arranged between said isothermal heat sink (under item B) and said heat radiator (under item C), wherein said Peltier heater cooler does transfer heat from said isothermal heat sink to said heat radiator or vice-versa.

2. The calibrating apparatus of claim 1 further comprising:

E) means for passing the dry gas through said moist gas generating unit;
F) means for controlling the flow rate of the dry gas;
G) means for controlling the temperature of said Peltier heater-cooler.

3. The apparatus of claim 2 wherein said isothermal heat sink is a metal body.

4. The apparatus of claim 3 wherein said heat radiator is made from metal.

5. The apparatus of claim 2, further comprising means for passing an electrical current through the Peltier heater-cooler in a first direction, in order to heat the moist gas generating unit.

6. The apparatus of claim 2, further comprising means for passing an electrical current through the Peltier heater-cooler in a second direction, in order to cool the moist gas generating unit.

7. A calibrating apparatus according to claim 2, particularly suitable for isothermally introducing calibrated amounts of moisture, lower than 10 and even 1 ppb, into a stream of dry gas, kept at superatmospheric pressure, wherein:

said permeation module, under item A/ii, is a tube, eccentric or coaxial with respect to said cylindrical shell under item A/i;

said thermal conditioner, under item A/iii, is consisting of an open porous structure, made from aluminum, thermally connected to said inside surface of said cylindrical shell;

said heat radiator, under item C) has a planar heat conducting surface parallel to and positioned a distance from the planar heat conducting surface of said isothermal heat sink;

said Peltier heater-cooler has a first and second parallel heat transfer surfaces thermally arranged between the isothermal heat sink and the radiator, with the first heat transfer surface in contact with the radiator and the second heat transfer surface in contact with the isothermal heat sink; wherein electrical current, passing through the Peltier heater-cooler in either of the two directions, heats one surface of the heater-cooler and cools the other surface of the heater-cooler or viceversa.

8. The apparatus of claim 7, further comprising means for passing an electrical current in either direction through said Peltier heater-cooler, thus accurately keeping the isothermal heat sink at a prefixed constant temperature level selected in a very wide range (from 0° C. to 70° C.).

9. The apparatus of claim 2, further comprising, upstream of said moist gas generating unit:

a) a source for said inlet gas;
b) subsequently a control valve and a mass flow controller;
c) subsequently a purifier filled with a molecular sieve material or with a getter material.

10. The apparatus of claim 9, further comprising means for by-passing said moist gas generating unit.

* * * * *